(12) United States Patent
Gu et al.

(10) Patent No.: US 10,745,515 B2
(45) Date of Patent: Aug. 18, 2020

(54) BIOMASS-BASED EPOXY RESIN AND PREPARATION METHOD THEREOF

(71) Applicant: SOOCHOW UNIVERSITY, Suzhou (CN)

(72) Inventors: Aijuan Gu, Suzhou (CN); Jiatao Miao, Suzhou (CN); Guozheng Liang, Suzhou (CN); Li Yuan, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 0 days.

(21) Appl. No.: 16/466,075

(22) PCT Filed: Dec. 3, 2016

(86) PCT No.: PCT/CN2016/108469
§ 371 (c)(1),
(2) Date: Jun. 3, 2019

(87) PCT Pub. No.: WO2018/098831
PCT Pub. Date: Jun. 7, 2018

(65) Prior Publication Data
US 2020/0062888 A1    Feb. 27, 2020

(51) Int. Cl.
*C08G 59/24*    (2006.01)
*C08G 59/68*    (2006.01)
*C08G 59/26*    (2006.01)
*C07D 307/68*    (2006.01)
*C07D 407/14*    (2006.01)
(Continued)

(52) U.S. Cl.
CPC .......... *C08G 59/24* (2013.01); *C07D 301/14* (2013.01); *C07D 303/02* (2013.01); *C07D 307/68* (2013.01); *C07D 407/14* (2013.01); *C08G 59/245* (2013.01); *C08G 59/26* (2013.01); *C08G 59/686* (2013.01)

(58) Field of Classification Search
CPC ...... C08G 59/00–72; C07D 301/03–19; C07D 303/02–32; C07D 307/00–76
See application file for complete search history.

(56) References Cited

FOREIGN PATENT DOCUMENTS

| CN | 105073846 A | 11/2015 |
| CN | 105924623 A | 9/2016 |
| FR | 3030514 A1 | 6/2016 |

*Primary Examiner* — Kregg T Brooks
(74) *Attorney, Agent, or Firm* — SZDC Law PC

(57) ABSTRACT

The present invention discloses a biomass-based epoxy resin and preparation method thereof; under conditions of N,N-dimethylformamide as a catalyst, 2,5-furandicarboxylic acid and thionyl chloride are acylated to obtain 2,5-furan diformyl chloride; then it is dissolved with dichloromethane; under tertiary amine conditions an esterification reaction takes place, and bis(4-allyl-2-methoxyphenyl)furan-2,5-dicarboxylic acid ester is thus obtained; by means of meta-chloroperoxybenzoic acid, its unsaturated double bond is epoxidized to obtain a biomass-based epoxy resin. The process of the present invention is simple; the raw materials come from biomass 2,5-furandicarboxylic acid and eugenol; in comparison with bisphenol-A epoxy resin based on petroleum and coal resources, the raw materials are green and renewable, and are advantageous to reducing the consumption of renewable resources with regard to polymeric material. The obtained cured epoxy resin has excellent thermal properties and modulus, and has broad prospects for application.

3 Claims, 4 Drawing Sheets

(51) Int. Cl.
*C07D 301/14* (2006.01)
*C07D 303/02* (2006.01)

US 10,745,515 B2

BIOMASS-BASED EPOXY RESIN AND PREPARATION METHOD THEREOF

This application is the National Stage Application of PCT/CN2016/108469, filed on Dec. 3, 2016.

FIELD OF THE INVENTION

The present invention relates to a biomass-based epoxy resin and its preparation method, in particular to a method for synthesizing a kind of fully biomass-based epoxy resin by using green and renewable biomass resources. It belongs to the technical field of chemical engineering and polymer materials.

BACKGROUND OF THE INVENTION

In recent years, due to the continuous reduction of petroleum and coal resource and the increasingly serious environmental pollution problems, the polymer materials industry which greatly depends on petroleum chemical industry is facing serious challenges. It is the most effective way to study green and renewable biomass material to replace petrochemical raw materials.

Biomass has the advantage of renewable, large annual production and wide distribution, but so far its utilization is very inefficient. How to efficiently convert renewable biomass resources into useful polymer materials has attracted great attention and interest from the whole world. Up to now, some biomass-based thermoplastics, such as polylactic acid, polyhydroxyalkanoate and the like, have been successfully synthesized and commercialized. However, there are few studies on biomass thermosetting resins compared to the rapid development of biomass thermoplastics.

Thermosetting resin is a kind of crosslinked polymer material with network structure, which has outstanding advantages such as superior strength, high heat resistance, good chemical resistance and excellent processability. It is widely used in coating, adhesives, electronic information and high performance composites and other fields.

Among the existing thermosetting resins, epoxy resin is widely used due to its excellent performance and low cost, accounting for about 70% of the thermosetting resin market, among which more than 90% is bisphenol A epoxy resin (DGEBA). The monomer of DGEBA is synthesized by bisphenol A and epichlorohydrin, both of which are based on petroleum and coal resources, under the condition of sodium hydroxide. Bisphenol A has a similar structure with estrogen, which reduces the fertility and is closely related to the increased risks of diseases and cancers. The US Federal Drug Administration has banned bisphenol A-based materials for packaging infant formula. Although the effects of bisphenol A on the endocrine system are still under study, the potential risks have led to the demand for bisphenol A-free products. At the same time, as bisphenol A is derived from petroleum and coal resources, under the premise of the continuous reduction of petroleum and coal resources, it is an urgent need for green renewable biomass epoxy resin raw materials to reduce the dependence of epoxy resin production on petroleum and coal resources.

In recent years, the literature reports on some biomass materials that replace DGEBA, such as vegetable oil, cardanol, itaconic acid, lignin and its derivatives. However, the biomass content of the synthesized epoxy resin cannot reach 100%, while there are shortcomings such as low reactivity of the epoxy resin system, poor mechanical properties of cured products, low glass transition temperature ($T_g$) and poor processability. Therefore, it is of great value to find an epoxy resin with high biomass content as well as excellent performance and its synthesis method.

Most of the biomass materials widely existed in nature is aliphatic compounds, which have poor thermal property. Therefore, eugenol and 2,5-furandicarboxylic acid stand out for their excellent thermal stability owing to their aromatic structure. 2,5-furandicarboxylic acid is listed as the top ten green chemical substances by U.S. Department of Energy. It is obtained by oxidation of 5-hydroxymethylfurfural (HMF), which can be obtained by dehydration of biomass-based C6 carbohydrates such as glucose, starch, cellulose and the like. Eugenol, accounting for about 80% of clove oil, is a renewable, low-toxic and relatively low-cost biomass material. Zhang et al. reported an epoxy resin based on eugenol with a biomass content of 62.7% (Ref: Jianglei Qin, Hongzhi Liu, Pei Zhang, Michael Wolcott and Jinwen Zhang. Polymer International, 2014, 63, 760-765). The cured product, prepared by using hexahydrophthalic anhydride as an epoxy curing agent, obtains a glass transition temperature ($T_g$) of only 114° C. Liu et al. reported an epoxy resin based on 2,5-furandicarboxylic acid (Ref: Jun Deng, Xiaoqing Liu, Chao Li, Yanhua Jiang and Jin Zhu. RSC advance, 2015, 5, 15930-15939), the cured product, taking hexahydrophthalic anhydride as a curing agent, has a $T_g$ value of 152° C., but its biomass content is only 65.2%. These studies indicate that the existing study on the use of biobased materials to synthesize epoxy resins cannot simultaneously have the properties of full biomass (100%), high thermal performance and high mechanical properties. This is because the raw materials for synthesizing epoxy resin in the prior art are not all biomass materials, resulting in that the biomass content of the synthetic resin is not high, and the selected materials do not have good thermal properties and the like.

SUMMARY OF THE INVENTION

Directed to the deficiencies of the prior art, the present invention provides a fully biomass epoxy resin based on green renewable resources and having outstanding thermal and mechanical properties and a preparation method thereof.

In order to achieve above purpose, the technical solution adopted by this invention is, A preparation method of a biomass-based epoxy resin, comprising the following steps:

(1) by mole, mixing 100 parts of 2,5-furandicarboxylic acid, 150 to 250 parts of thionyl chloride and a catalytic amount of N,N-dimethylformamide and stirring to react at a temperature of 70 to 80° C. for 3 to 5 h, naturally cooling to room temperature, removing thionyl chloride by vacuum distillation, after drying to obtain 2,5-furodicarboxylic acid chloride;

(2) by mole, dissolving 190 to 210 parts of eugenol and 240 to 300 parts of tertiary amine in 3120 to 7800 parts of dichloromethane solvent to obtain eugenol solution; at a temperature of −5 to 0° C., adding a solution by 100 parts of 2,5-furan dicarboxylic acid chloride dissolved in 3120 to 7800 parts of dichloromethane dropwise in said eugenol solution, after completion of dropwise addition, heating the reaction solution slowly to the temperature of 20 to 30° C., and continuing the reaction for 2 to 4 h; and then removing dichloromethane under vacuum rotary evaporation, washing and drying to obtain bis(4-allyl-2-methoxyphenyl)furan-2,5-dicarboxylate;

(3) by mole, dissolving 100 parts of bis(4-allyl-2-methoxyphenyl)-furan-2,5-dicarboxylate in 4680 to 9360 parts of dichloromethane, then slowly adding 300 to 400 parts of metachloroperbenzoic acid in under stirring at the temperature of 20 to 30° C., continuing to react for 2 to 4 days, and then a filtrate is obtained after filtration; washing and removing the solvent in the filtrate, and then washing again to obtain a white solid, which is the biomass-based epoxy resin.

In the present invention, said tertiary amine is one of triethylamine, N-ethyl diisopropylamine, pyridine, or any combination thereof.

The present invention also discloses a biomass-based epoxy resin obtained by above preparation method.

Compared with the prior arts, this invention has following advantages:

1. In this invention, a special fully biomass-based epoxy resin is synthesized with biobased renewable eugenol and 2,5-furandicarboxylic acid as raw materials; its biomass content is as high as 100%. Both of the raw materials are green and low toxic materials.

2. In this invention, the epoxy resin provided has aromatic skeleton, excellent thermal and mechanical properties.

3. In this invention, the preparation method of the fully biomass-based epoxy resin is green and environmental protected with simple preparation process, good processing controllability and is easy to be industrialized.

DETAILED DESCRIPTION OF THE INVENTION

The technical solution of this invention will be further described below with the accompanying figures and examples.

Example 1

1) Synthesis of 2,5-Furan Dicarboxylic Acid Chloride 31.20 g 2,5-Furandicarboxylic acid, 35.69 g thionyl chloride and N,N-dimethylformamide (DMF, catalyst, 0.05 mL) are mixed; the reaction is carried out for 3 h at 80° C. with stirring, and then the mixture is naturally cooled to room temperature. After removing the thionyl chloride under reduced pressure and drying, 2,5-furan dicarboxylic acid chloride is obtained.

Figure 1:
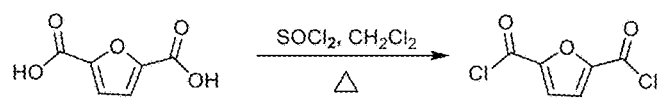
FIG. 1 is synthesis of 2,5-furan dicarboxylic acid chloride in the example 1.

As shown in FIG. 1, it gives the synthesis reaction formula of 2,5-furan dicarboxylic acid chloride of this invention;

2) Synthesis of Fully Biobased bis(4-allyl-2-methoxyphenyl)furan-2,5-dicarboxylate 31.20 g Eugenol and 24.29 g triethylamine acting as base are dissolved in 200 mL dichloromethane to make solution A; at the temperature ranging from −5 to 0° C., 2,5-furan dicarboxylic acid chloride (19.30 g) is dissolved in 200 mL dichloromethane to get 2,5-furan dicarboxylic acid chloride solution, which is then slowly dropped into solution A; After dropwise addition is completed, the reaction solution is slowly heated and maintained at 20° C. for 2 h; after the reaction is over, removing the solvent under reduced pressure, followed by washing with deionized water and drying, successively, a fully biobased bis(4-allyl-2-methoxyphenyl) furan-2,5-dicarboxylate is obtained.

Figure 2:
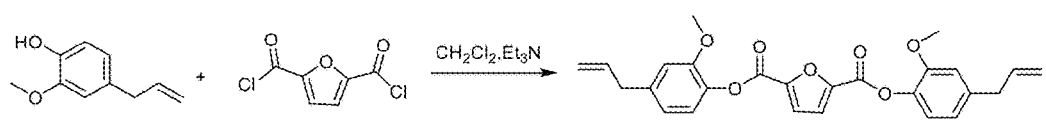
FIG. 2 is synthesis of bis(4-allyl-2-methoxyphenyl)furan-2,5-dicarboxylate.
Figure 3:
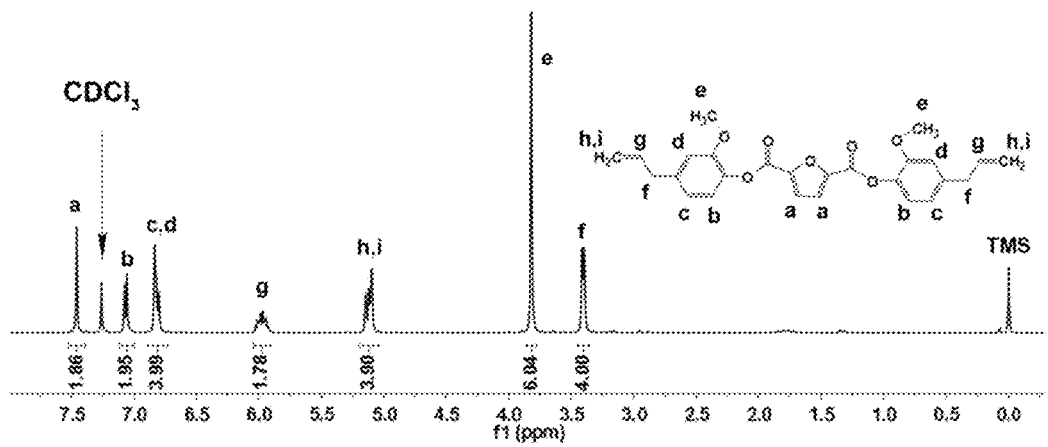
FIG. 3 is the $^1$H-NMR spectrum of bis(4-allyl-2-methoxyphenyl) furan-2,5-dicarboxylate prepared in Example 1 of this invention.

The reaction equation and $^1$H-NMR spectra of the fully biobased bis(4-allyl-2-methoxyphenyl)furan-2,5-dicarboxylate obtained in this example are shown in FIG. 2 and FIG. 3, respectively.

FIG. 1 shows the reaction scheme (reaction equation) for synthesizing the intermediate 2,5-furan dicarboxylic acid chloride provided by this example, the reaction is a carboxylic acid acyl chloride reaction. FIG. 2 shows, the reaction scheme (reaction equation) for synthesizing fully biobased bis(4-allyl-2-methoxyphenyl)furan-2,5-dicarboxylate in this example, the reaction is an esterification reaction.

FIG. 3 shows the $^1$H-NMR spectrum of fully biobased bis(4-allyl-2-methoxy-phenyl)furan-2,5-dicarboxylate obtained in Example 1 of this invention. It can be seen that the peaks at 5.98 ppm and 5.04~5.20 ppm represent protons of allyl groups, the peak at 3.40 ppm represents the proton of methylene groups adjacent to the double bond of allyl groups, the peak at 3.82 ppm represents the proton of methoxy groups, the peak at 7.43 ppm represents the proton of furan rings, other peaks match with the chemical shifts of protons of the biobased allyl compound.

3) Preparation of the Biobased Epoxy Resin 22.42 g Bis(4-allyl-2-methoxyphenyl)furan-2,5-dicarboxylate is dissolved in 150 mL dichloromethane, then 30.45 g metachloroperbenzoic acid (85 wt %) is slowly added under stirring at 20° C. The reaction kept for 2 days, and then a filtrate is obtained after filtration, which is then washed with 63.02 g 10% $Na_2SO_3$, 53.00 g 10% $Na_2CO_3$ and deionized water, successively; the organic layer is obtained by separating and dried over anhydrous sodium sulfate; dichloromethane is removed to obtain a yellow solid which is washed by diethyl ether to get a white solid. The reaction equation, $^1$H-NMR, $^{13}$C-NMR and high resolution mass spectra of the biobased epoxy resin obtained in this example are shown in FIGS. 4, 5, 6, 7 and 8, respectively.

Figure 4:
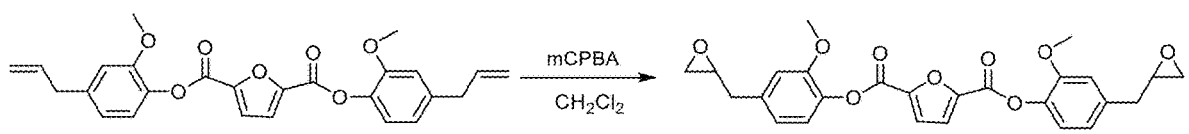
FIG. 4 is synthesis of fully biobased epoxy resin prepared in Example 1 of this invention.
Figure 5:
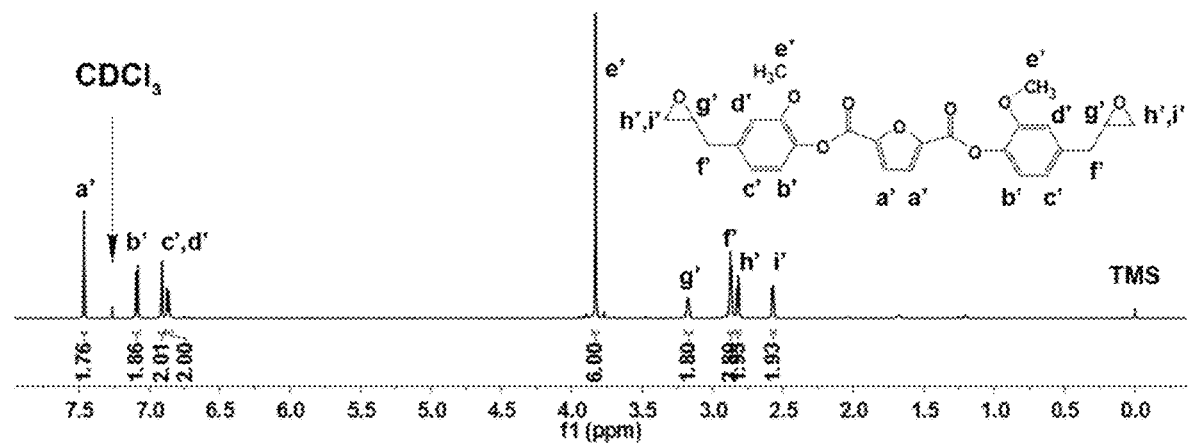
FIG. 5 is the $^1$H-NMR spectrum of fully biobased epoxy resin prepared in Example 1 of this invention.

FIG. 4 shows the reaction scheme (reaction equation) for the synthesis of the biobased epoxy resin provided by this example, the reaction is an epoxidation of double bonds As shown in FIG. 5, it is the $^1$H-NMR spectrum of the biobased epoxy resin provided by Example 1 in this invention. It can be seen that, the characteristic peaks at 5.98 ppm and 5.08-5.16 ppm corresponding to protons on double bonds of allyl groups are not found, while the characteristic peaks of proton on epoxy group are observed (2.57 ppm, 2.80-2.84 ppm, 3.14-3.20 ppm), other peaks reflect protons on biobased epoxy resin, indicating that the expected compound has been successfully synthesized.

Figure 6:
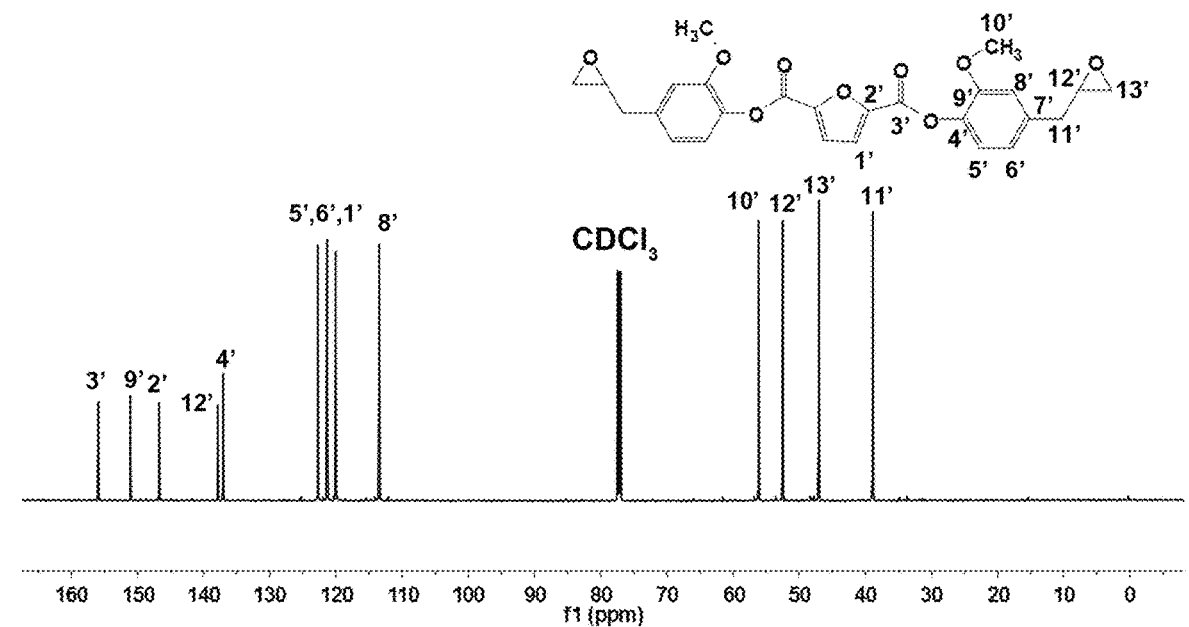
FIG. 6 is the $^{13}$C-NMR spectrum of fully biobased epoxy resin prepared in Example 1 of this invention.

As shown in FIG. 6, it is the $^{13}$C-NMR spectrum of the biobased epoxy resin provided by Example 1 in this invention. Characteristic peaks representing carbon atoms on epoxy groups appear at 52.46 ppm and 47.00 ppm.

Figure 7:
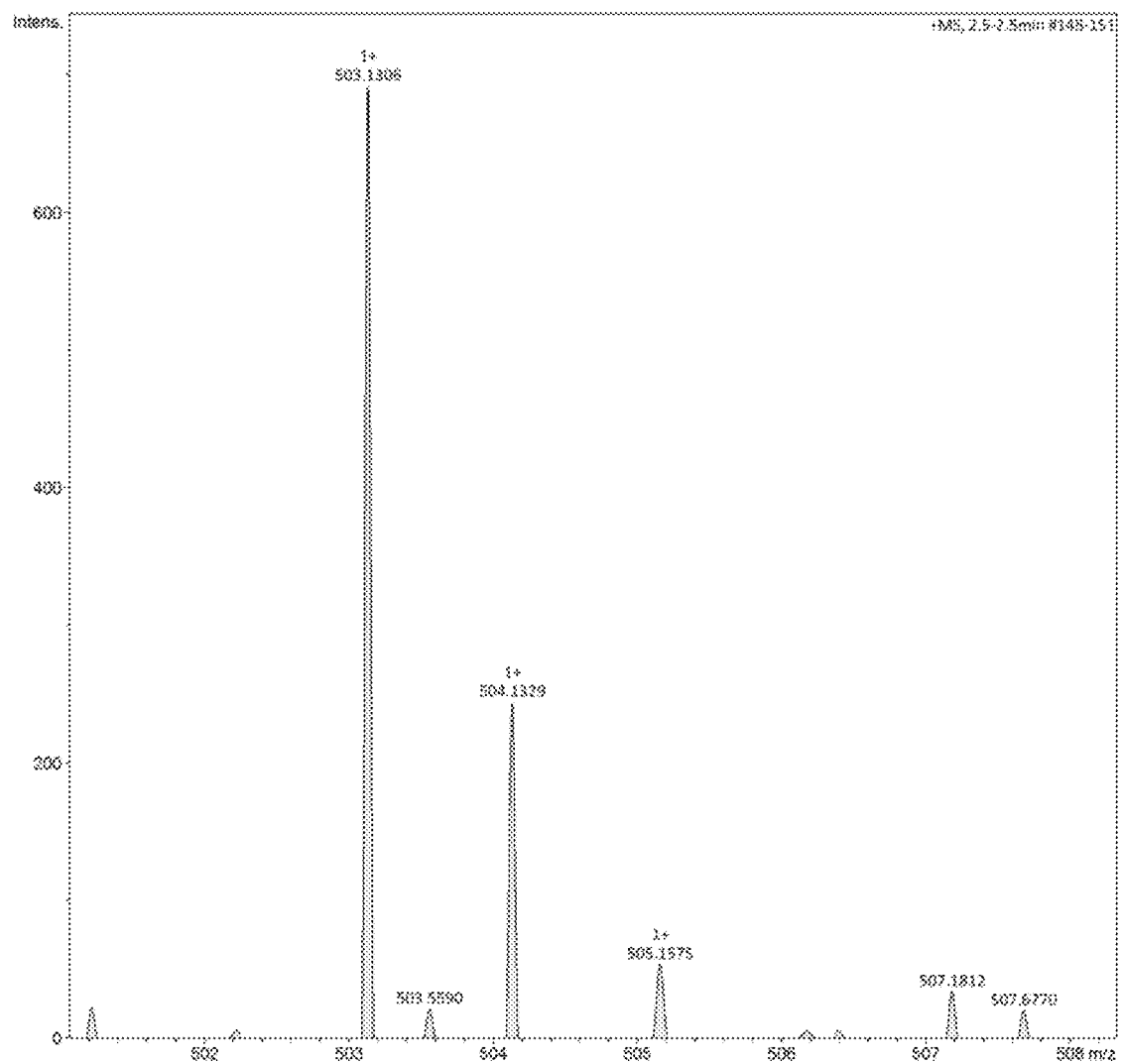
FIG. 7 is the high resolution mass spectrum of fully biobased epoxy resin prepared in Example 1 of this invention.

As shown in FIG. 7, it is the high resolution mass spectrometry of the biobased epoxy resin provided by Example 1 in this invention. Its theoretical molecular weight [M] is 480.1420, the theoretical value of [M+Na$^+$] is 503.1313, which is well agreed with the experimental value (503.1306).

Based on above figures, it is reasonable to state that the target fully biobased epoxy resin is synthesized in Example 1 of this invention.

Control Example 1, Preparation of Biobased Epoxy Resin:

The biobased epoxy resin provided by Example 1 (9.6 g), methylhexahydrophthalic anhydride (curing agent, 6.7 g) and 2-ethylmethylimidazole (accelerator, 81.7 g) are mixed uniformly, and then precured at a constant temperature of 80° C. for 30 min to get a prepolymer; the prepolymer is poured into a preheated glass mold and degassed under vacuum at 80° C. for 30 min, followed by curing with the procedure of 130° C./2 h+150° C./2 h+170° C./2 h; after natural cooling to room temperature and demolding, the cured biobased epoxy resin is obtained. Its storage modulus-temperature curve is shown in FIG. 8.

Control Example 2, Preparation of DGEBA Resin:

DGEBA (its trademark is E44, epoxide equivalent is 210-240 g/eq, 10.0 g), methylhexahydrophthalic anhydride (7.4 g) and 2-ethylmethylimidazole (accelerator, 87.0 g) are mixed uniformly, and then precured at a constant temperature of 80° C. for 30 min; the prepolymer is poured into a preheated glass mold and degassed under vacuum at 80° C. for 30 min to get a prepolymer, followed by curing with the procedure of 130° C./2 h+150° C./2 h+170° C./2 h; after natural cooling to room temperature and demolding, the cured DGEBA resin is obtained. Its storage modulus-temperature curve is shown in FIG. 8.

Figure 8:
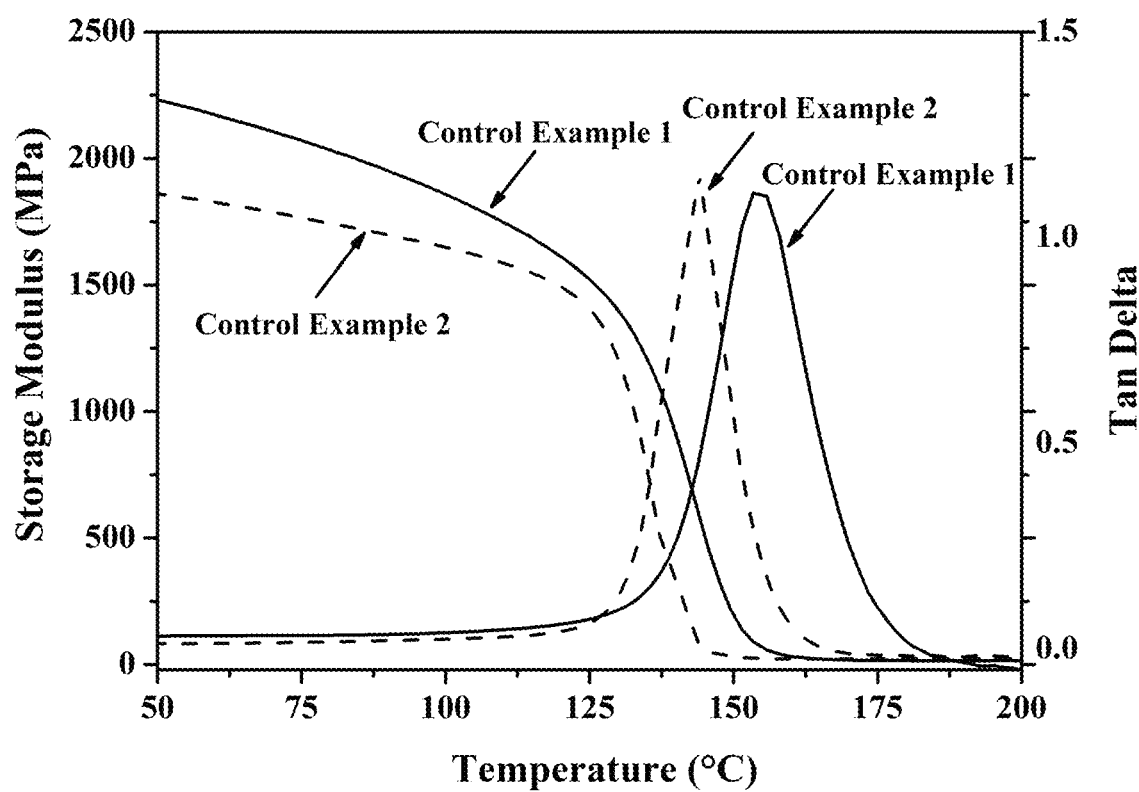
FIG. 8 is dynamic mechanical analyses (DMA) curves of fully biobased epoxy resin prepared in Example 1 and DGEBA prepared in Control Example 2 of this invention.

As shown in FIG. 8, it is DMA curves of the biobased epoxy resin prepared in Control Example 1 and the DGEBA resin prepared in Control Example 2 of this invention. It can be seen that, the storage modulus of epoxy resin prepared in Control Example 1 at 50° C. is 2229 MPa, 19.9% higher than that of DGEBA resin prepared in Control Example 2 (1860 MPa). $T_g$ of the epoxy resin provided in Control Example 1 is 153.4° C., while that of DGEBA resin prepared in Comparative Example 2 is 144.1° C. The figure demonstrates that the biobased epoxy resin provided in this invention has a high modulus and $T_g$ after curing. This is due to the fact that there is furan group in the chemical structure of the biobased epoxy resin-based provided by this invention, which can improve the rigidity and heat resistance of epoxy resins.

Example 2

1) Synthesis of 2,5-Furan Dicarboxylic Acid Chloride 31.20 g 2,5-Furandicarboxylic acid, 35.69 g thionyl chloride and N,N-dimethylformamide (DMF, catalyst, 0.05 mL) are mixed; the reaction is carried out for 3 h at 80° C. with stirring, and then the mixture is naturally cooled to room temperature. After removing the thionyl chloride under reduced pressure and drying, 2,5-furan dicarboxylic acid chloride is obtained.

2) Synthesis of Fully Biobased bis(4-allyl-2-methoxyphenyl)furan-2,5-dicarboxylate 32.84 g Eugenol and 27.33 g triethylamine acting as base are dissolved in 300 mL dichloromethane to make solution A; at the temperature range of −2.5±1° C., 2,5-furan dicarboxylic acid chloride (19.30 g) is dissolved in 300 mL dichloromethane solution to get 2,5-furan dicarboxylic acid chloride solution, which is then slowly dropped into solution A; After dropwise addition is completed, the reaction solution is slowly heated and maintained at 20° C. for 3 h; after the reaction is over, removing the solvent under reduced pressure, followed by washing with deionized water and drying, successively, a fully biobased bis(4-allyl-2-methoxyphenyl)furan-2,5-dicarboxylate is obtained.

3) Preparation of the Biobased Epoxy Resin 22.42 g Bis(4-allyl-2-methoxyphenyl)furan-2,5-dicarboxylate is dissolved in 225 mL dichloromethane, then 35.5 g metachloroperbenzoic acid (85 wt %) is slowly added under stirring at 25° C. The reaction kept for 3 days, and then a filtrate is obtained after filtration, which is then washed with 84.03 g 10% $Na_2SO_3$, 70.66 g 10% $Na_2CO_3$ and deionized water successively; the organic layer is obtained by separating and dried over anhydrous sodium sulfate; dichloromethane is removed to obtain a yellow solid which is washed by diethyl ether to get a white solid.

Example 3

1) Synthesis of 2,5-Furan Dicarboxylic Acid Chloride 31.20 g 2,5-Furandicarboxylic acid, 35.69 g thionyl chloride and N,N-dimethylformamide (DMF, catalyst, 0.05 mL) are mixed; the reaction is carried out for 3 h at 70° C. with stirring, and then the mixture is naturally cooled to room temperature. After removing the thionyl chloride under reduced pressure and drying, 2,5-furan dicarboxylic acid chloride is obtained.

2) Synthesis of Fully Biobased bis(4-allyl-2-methoxyphenyl)furan-2,5-dicarboxylate 34.48 g Eugenol and 30.36 g triethylamine acting as base are dissolved in 500 mL dichloromethane to make solution A; at the temperature range of −1±1° C., 2,5-furan dicarboxylic acid chloride (19.30 g) is dissolved in 500 mL dichloromethane solution to get 2,5-furan dicarboxylic acid chloride solution, which is then slowly dropped into solution A; After dropwise addition is completed, the reaction solution is slowly heated and maintained at 20° C. for 2 h; after the reaction is over, removing the solvent under reduced pressure, followed by washing with deionized water and drying, successively, a fully biobased bis(4-allyl-2-methoxyphenyl)furan-2,5-dicarboxylate is obtained.

Example 4

1) Synthesis of 2,5-Furan Dicarboxylic Acid Chloride 31.20 g 2,5-Furandicarboxylic acid, 35.69 g thionyl chloride and N,N-dimethylformamide (DMF, catalyst, 0.05 mL) are mixed; the reaction is carried out for 3 h at 70° C. with stirring, and then the mixture is naturally cooled to room temperature. After removing the thionyl chloride under reduced pressure and drying, 2,5-furan dicarboxylic acid chloride is obtained.

2) Synthesis of Fully Biobased bis(4-allyl-2-methoxyphenyl)furan-2,5-dicarboxylate 31.20 g Eugenol and 31.03 g triethylamine acting as base are dissolved in 300 mL dichloromethane to make solution A; at the temperature range of −4±1° C., 2,5-furan dicarboxylic acid chloride (19.30 g) is dissolved in 200 mL dichloromethane solution to get 2,5-furan dicarboxylic acid chloride solution, which is then slowly dropped into solution A; After dropwise addition is completed, the reaction solution is slowly heated and maintained at 20° C. for 2 h; after the reaction is over, removing the solvent under reduced pressure, followed by washing with deionized water and drying, successively, a fully biobased bis(4-allyl-2-methoxyphenyl)furan-2,5-dicarboxylate is obtained.

3) Preparation of the Biobased Epoxy Resin 22.42 g Bis(4-allyl-2-methoxyphenyl)furan-2,5-dicarboxylate is dissolved in 150 mL dichloromethane, then 30.45 g metachloroperbenzoic acid (85 wt %) is slowly added under stirring at 20° C. The reaction kept for 2 days, and then a filtrate is obtained after filtration, which is then washed with 63.02 g 10% $Na_2SO_3$, 53.00 g 10% $Na_2CO_3$ and deionized water successively; the organic layer is obtained by separating and dried over anhydrous sodium sulfate; dichloromethane is removed to obtain a yellow solid which is washed by diethyl ether to get a white solid.

Example 5

1) Synthesis of 2,5-Furan Dicarboxylic Acid Chloride 31.20 g 2,5-Furandicarboxylic acid, 35.69 g thionyl chloride and N,N-dimethylformamide (DMF, catalyst, 0.05 mL) are mixed; the reaction is carried out for 3 h at 70° C. with stirring, and then the mixture is naturally cooled to room temperature. After removing the thionyl chloride under reduced pressure and drying, 2,5-furan dicarboxylic acid chloride is obtained.

2) Synthesis of Fully Biobased bis(4-allyl-2-methoxyphenyl)furan-2,5-dicarboxylate 34.48 g Eugenol and 23.73 g triethylamine acting as base are dissolved in 500 mL dichloromethane to make solution A; at the temperature range of −1±1° C., 2,5-furan dicarboxylic acid chloride (19.30 g) is dissolved in 500 mL dichloromethane solution to get 2,5-furan dicarboxylic acid chloride solution, which is then slowly dropped into solution A; After dropwise addition is completed, the reaction solution is slowly heated and maintained at 20° C. for 4 h; after the reaction is over, removing the solvent under reduced pressure, followed by washing with deionized water and drying, successively, a fully biobased bis(4-allyl-2-methoxyphenyl)furan-2,5-dicarboxylate is obtained.

3) Preparation of the Biobased Epoxy Resin 22.42 g Bis(4-allyl-2-methoxyphenyl)furan-2,5-dicarboxylate is dissolved in 225 mL dichloromethane, then 35.5 g metachloroperbenzoic acid (85 wt %) is slowly added under stirring at 25° C. The reaction kept for 3 days, and then a filtrate is obtained after filtration, which is then washed with 84.03 g 10% $Na_2SO_3$, 70.66 g 10% $Na_2CO_3$ and deionized water successively; the organic layer is obtained by separating and dried over anhydrous sodium sulfate; dichloromethane is removed to obtain a yellow solid which is washed by diethyl ether to get a white solid.

Example 6

1) Synthesis of 2,5-Furan Dicarboxylic Acid Chloride 31.20 g 2,5-Furandicarboxylic acid, 47.59 g thionyl chloride and N,N-dimethylformamide (DMF, catalyst, 0.05 mL) are mixed; the reaction is carried out for 4 h at 75° C. with stirring, and then the mixture is naturally cooled to room temperature. After removing the thionyl chloride under reduced pressure and drying, 2,5-furan dicarboxylic acid chloride is obtained.

2) Synthesis of Fully Biobased bis(4-allyl-2-methoxyphenyl)furan-2,5-dicarboxylate 31.20 g Eugenol and 24.29 g triethylamine acting as base are dissolved in 200 mL dichloromethane to make solution A; at the temperature ranging from −5 to 0° C., 2,5-furan dicarboxylic acid chloride (19.30 g) is dissolved in 200 mL dichloromethane solution to get 2,5-furan dicarboxylic acid chloride solution, which is then slowly dropped into solution A; After dropwise addition is completed, the reaction solution is slowly heated and maintained at 25° C. for 2 h; after the reaction is over, removing the solvent under reduced pressure, followed by washing with deionized water and drying, successively, a fully biobased bis(4-allyl-2-methoxyphenyl)furan-2,5-dicarboxylate is obtained.

3) Preparation of the Biobased Epoxy Resin 22.42 g Bis(4-allyl-2-methoxyphenyl)furan-2,5-dicarboxylate is dissolved in 300 mL dichloromethane, then 40.6 g metachloroperbenzoic acid (85 wt %) is slowly added under stirring at 30° C. The reaction kept for 4 days, and then a filtrate is obtained after filtration, which is then washed with 126.04 g 10% $Na_2SO_3$, 105.99 g 10% $Na_2CO_3$ and deionized water successively; the organic layer is obtained by separating and dried over anhydrous sodium sulfate; dichloromethane is removed to obtain a yellow solid which is washed by diethyl ether to get a white solid.

Example 7

1) Synthesis of 2,5-Furan Dicarboxylic Acid Chloride 31.20 g 2,5-Furandicarboxylic acid, 47.59 g thionyl chloride and N,N-dimethylformamide (DMF, catalyst, 0.05 mL) are mixed; the reaction is carried out for 4 h at 75° C. with stirring, and then the mixture is naturally cooled to room temperature. After removing the thionyl chloride under reduced pressure and drying, 2,5-furan dicarboxylic acid chloride is obtained.

2) Synthesis of Fully Biobased bis(4-allyl-2-methoxyphenyl)furan-2,5-dicarboxylate 32.84 g Eugenol and 27.33 g triethylamine acting as base are dissolved in 300 mL dichloromethane to make solution A; at the temperature range of −2.5±1° C., 2,5-furan dicarboxylic acid chloride (19.30 g) is dissolved in 300 mL dichloromethane solution to get 2,5-furan dicarboxylic acid chloride solution, which is then slowly dropped into solution A; After dropwise addition is completed, the reaction solution is slowly heated and maintained at 25° C. for 3 h; after the reaction is over, removing the solvent under reduced pressure, followed by washing with deionized water and drying, successively, a fully biobased bis(4-allyl-2-methoxyphenyl)furan-2,5-dicarboxylate is obtained.

3) Preparation of the Biobased Epoxy Resin 22.42 g Bis(4-allyl-2-methoxyphenyl)furan-2,5-dicarboxylate is dissolved in 150 mL dichloromethane, then 30.45 g metachloroperbenzoic acid (85 wt %) is slowly added under stirring at 20° C. The reaction kept for 2 days, and then a filtrate is obtained after filtration, which is then washed with 63.02 g 10% $Na_2SO_3$, 53.00 g 10% $Na_2CO_3$ and deionized water successively; the organic layer is obtained by separating and dried over anhydrous sodium sulfate; dichloromethane is removed to obtain a yellow solid which is washed by diethyl ether to get a white solid.

Example 8

1) Synthesis of 2,5-Furan Dicarboxylic Acid Chloride 31.20 g 2,5-Furandicarboxylic acid, 47.59 g thionyl chloride and N,N-dimethylformamide (DMF, catalyst, 0.05 mL) are mixed; the reaction is carried out for 4 h at 75° C. with stirring, and then the mixture is naturally cooled to room temperature. After removing the thionyl chloride under reduced pressure and drying, 2,5-furan dicarboxylic acid chloride is obtained.

2) Synthesis of Fully Biobased bis(4-allyl-2-methoxyphenyl)furan-2,5-dicarboxylate 34.48 g Eugenol and 30.36 g triethylamine acting as base are dissolved in 500 mL dichloromethane to make solution A; at the temperature range of −1±1° C., 2,5-furan dicarboxylic acid chloride (19.30 g) is dissolved in 500 mL dichloromethane solution to get 2,5-furan dicarboxylic acid chloride solution, which is then slowly dropped into solution A; After dropwise addition is completed, the reaction solution is slowly heated and maintained at 25° C. for 4 h; after the reaction is over, removing the solvent under reduced pressure, followed by washing with deionized water and drying, successively, a fully biobased bis(4-allyl-2-methoxyphenyl)furan-2,5-dicarboxylate is obtained.

3) Preparation of the Biobased Epoxy Resin 22.42 g Bis(4-allyl-2-methoxyphenyl)furan-2,5-dicarboxylate is dissolved in 225 mL dichloromethane, then 35.5 g metachloroperbenzoic acid (85 wt %) is slowly added under stirring at 20° C. The reaction kept for 2 days, and then a filtrate is obtained after filtration, which is then washed with 84.03 g 10% $Na_2SO_3$, 70.66 g 10% $Na_2CO_3$ and deionized water successively; the organic layer is obtained by separating and dried over anhydrous sodium sulfate; dichloromethane is removed to obtain a yellow solid which is washed by diethyl ether to get a white solid.

Example 9

1) Synthesis of 2,5-Furan Dicarboxylic Acid Chloride 31.20 g 2,5-Furandicarboxylic acid, 31.03 g thionyl chloride and N,N-dimethylformamide (DMF, catalyst, 0.05 mL) are mixed; the reaction is carried out for 4 h at 75° C. with stirring, and then the mixture is naturally cooled to room temperature. After removing the thionyl chloride under reduced pressure and drying, 2,5-furan dicarboxylic acid chloride is obtained.

2) Synthesis of Fully Biobased bis(4-allyl-2-methoxyphenyl)furan-2,5-dicarboxylate 31.20 g Eugenol and 31.03 g triethylamine acting as base are dissolved in 200 mL dichloromethane to make solution A; at the temperature range of −4±1° C., 2,5-furan dicarboxylic acid chloride (19.30 g) is dissolved in 200 mL dichloromethane solution to get 2,5-furan dicarboxylic acid chloride solution, which is then slowly dropped into solution A; After dropwise addition is completed, the reaction solution is slowly heated and maintained at 25° C. for 2 h; after the reaction is over, removing the solvent under reduced pressure, followed by washing with deionized water and drying, successively, a fully biobased bis(4-allyl-2-methoxyphenyl)furan-2,5-dicarboxylate is obtained.

3) Preparation of the Biobased Epoxy Resin 22.42 g Bis(4-allyl-2-methoxyphenyl)furan-2,5-dicarboxylate is dissolved in 300 mL dichloromethane, then 40.6 g metachloroperbenzoic acid (85 wt %) is slowly added under stirring at 30° C. The reaction kept for 4 days, and then a filtrate is obtained after filtration, which is then washed with 126.04 g 10% $Na_2SO_3$, 105.99 10% $Na_2CO_3$ and deionized water successively; the organic layer is obtained by separating and dried over anhydrous sodium sulfate; dichloromethane is removed to obtain a yellow solid which is washed by diethyl ether to get a white solid.

Example 10

1) Synthesis of 2,5-Furan Dicarboxylic Acid Chloride 31.20 g 2,5-Furandicarboxylic acid, 47.59 g thionyl chloride and N,N-dimethylformamide (DMF, catalyst, 0.05 mL) are mixed; the reaction is carried out for 4 h at 75° C. with stirring, and then the mixture is naturally cooled to room temperature. After removing the thionyl chloride under reduced pressure and drying, 2,5-furan dicarboxylic acid chloride is obtained.

2) Synthesis of Fully Biobased bis(4-allyl-2-methoxyphenyl)furan-2,5-dicarboxylate 34.48 g Eugenol and 23.73 g triethylamine acting as base are dissolved in 500 mL dichloromethane to make solution A; at the temperature range of −1±1° C., 2,5-furan dicarboxylic acid chloride (19.30 g) is dissolved in 500 mL dichloromethane solution to get 2,5-furan dicarboxylic acid chloride solution, which is then slowly dropped into solution A; After dropwise addition is completed, the reaction solution is slowly heated and maintained at 25° C. for 4 h; after the reaction is over, removing the solvent under reduced pressure, followed by washing with deionized water and drying, successively, a fully biobased bis(4-allyl-2-methoxyphenyl)furan-2,5-dicarboxylate is obtained.

3) Preparation of the Biobased Epoxy Resin 22.42 g Bis(4-allyl-2-methoxyphenyl)furan-2,5-dicarboxylate is dissolved in 150 mL dichloromethane, then 30.45 g metachloroperbenzoic acid (85 wt %) is slowly added under stirring at 20° C. The reaction kept for 2 days, and then a filtrate is obtained after filtration, which is then washed with 63.02 g 10% $Na_2SO_3$, 53.00 g 10% $Na_2CO_3$ and deionized water successively; the organic layer is obtained by separating and dried over anhydrous sodium sulfate; dichloromethane is removed to obtain a yellow solid which is washed by diethyl ether to get a white solid.

Example 11

1) Synthesis of 2,5-Furan Dicarboxylic Acid Chloride 31.20 g 2,5-Furandicarboxylic acid, 59.48 g thionyl chloride and N,N-dimethylformamide (DMF, catalyst, 0.05 mL) are mixed; the reaction is carried out for 5 h at 80° C. with stirring, and then the mixture is naturally cooled to room temperature. After removing the thionyl chloride under reduced pressure and drying, 2,5-furan dicarboxylic acid chloride is obtained.

2) Synthesis of Fully Biobased bis(4-allyl-2-methoxyphenyl)furan-2,5-dicarboxylate 31.20 g Eugenol and 24.29 g triethylamine acting as base are dissolved in 200 mL dichloromethane to make solution A; at the temperature ranging from −5 to 0° C., 2,5-furan dicarboxylic acid chloride (19.30 g) is dissolved in 200 mL dichloromethane solution to get 2,5-furan dicarboxylic acid chloride solution, which is then slowly dropped into solution A; After dropwise addition is completed, the reaction solution is slowly heated and maintained at 30° C. for 2 h; after the reaction is over, removing the solvent under reduced pressure, followed by washing with deionized water and drying, successively, a fully biobased bis(4-allyl-2-methoxyphenyl)furan-2,5-dicarboxylate is obtained.

3) Preparation of the Biobased Epoxy Resin 22.42 g Bis(4-allyl-2-methoxyphenyl)furan-2,5-dicarboxylate is dissolved in 225 mL dichloromethane, then 35.5 g metachloroperbenzoic acid (85 wt %) is slowly added under stirring at 25° C. The reaction kept for 3 days, and then a filtrate is obtained after filtration, which is then washed with 84.03 g 10% $Na_2SO_3$, 70.66 g 10% $Na_2CO_3$ and deionized water successively; the organic layer is obtained by separating and dried over anhydrous sodium sulfate; dichloromethane is removed to obtain a yellow solid which is washed by diethyl ether to get a white solid.

Example 12

1) Synthesis of 2,5-Furan Dicarboxylic Acid Chloride 31.20 g 2,5-Furandicarboxylic acid, 59.48 g thionyl chloride and N,N-dimethylformamide (DMF, catalyst, 0.05 mL)

are mixed; the reaction is carried out for 5 h at 80° C. with stirring, and then the mixture is naturally cooled to room temperature. After removing the thionyl chloride under reduced pressure and drying, 2,5-furan dicarboxylic acid chloride is obtained.

2) Synthesis of Fully Biobased bis(4-allyl-2-methoxyphenyl)furan-2,5-dicarboxylate 32.84 g Eugenol and 27.33 g triethylamine acting as base are dissolved in 300 mL dichloromethane to make solution A; at the temperature range of −2.5±1° C., 2,5-furan dicarboxylic acid chloride (19.30 g) is dissolved in 300 mL dichloromethane solution to get 2,5-furan dicarboxylic acid chloride solution, which is then slowly dropped into solution A; After dropwise addition is completed, the reaction solution is slowly heated and maintained at 30° C. for 3 h; after the reaction is over, removing the solvent under reduced pressure, followed by washing with deionized water and drying, successively, a fully biobased bis(4-allyl-2-methoxyphenyl)furan-2,5-dicarboxylate is obtained.

3) Preparation of the Biobased Epoxy Resin 22.42 g Bis(4-allyl-2-methoxyphenyl)furan-2,5-dicarboxylate is dissolved in 300 mL dichloromethane, then 40.6 g metachloroperbenzoic acid (85 wt %) is slowly added under stirring at 30° C. The reaction kept for 4 days, and then a filtrate is obtained after filtration, which is then washed with 126.04 g 10% $Na_2SO_3$, 105.99 g 10% $Na_2CO_3$ and deionized water successively; the organic layer is obtained by separating and dried over anhydrous sodium sulfate; dichloromethane is removed to obtain a yellow solid which is washed by diethyl ether to get a white solid.

Example 13

1) Synthesis of 2,5-Furan Dicarboxylic Acid Chloride 31.20 g 2,5-Furandicarboxylic acid, 59.48 g thionyl chloride and N,N-dimethylformamide (DMF, catalyst, 0.05 mL) are mixed; the reaction is carried out for 5 h at 80° C. with stirring, and then the mixture is naturally cooled to room temperature. After removing the thionyl chloride under reduced pressure and drying, 2,5-furan dicarboxylic acid chloride is obtained.

2) Synthesis of Fully Biobased bis(4-allyl-2-methoxyphenyl)furan-2,5-dicarboxylate 34.48 g Eugenol and 30.36 g triethylamine acting as base are dissolved in 500 mL dichloromethane to make solution A; at the temperature range of −1±1° C., 2,5-furan dicarboxylic acid chloride (19.30 g) is dissolved in 500 mL dichloromethane solution to get 2,5-furan dicarboxylic acid chloride solution, which is then slowly dropped into solution A; After dropwise addition is completed, the reaction solution is slowly heated and maintained at 30° C. for 4 h; after the reaction is over, removing the solvent under reduced pressure, followed by washing with deionized water and drying, successively, a fully biobased bis(4-allyl-2-methoxyphenyl)furan-2,5-dicarboxylate is obtained.

3) Preparation of the Biobased Epoxy Resin 22.42 g Bis(4-allyl-2-methoxyphenyl)furan-2,5-dicarboxylate is dissolved in 150 mL dichloromethane, then 30.45 g metachloroperbenzoic acid (75 wt %) is slowly added under stirring at 20° C. The reaction kept for 2 days, and then a filtrate is obtained after filtration, which is then washed with 63.02 g 10% $Na_2SO_3$, 53.00 g 10% $Na_2CO_3$ and deionized water successively; the organic layer is obtained by separating and dried over anhydrous sodium sulfate; dichloromethane is removed to obtain a yellow solid which is washed by diethyl ether to get a white solid.

Example 14

1) Synthesis of 2,5-Furan Dicarboxylic Acid Chloride 31.20 g 2,5-Furandicarboxylic acid, 59.48 g thionyl chloride and N,N-dimethylformamide (DMF, catalyst, 0.05 mL) are mixed; the reaction is carried out for 5 h at 80° C. with stirring, and then the mixture is naturally cooled to room temperature. After removing the thionyl chloride under reduced pressure and drying, 2,5-furan dicarboxylic acid chloride is obtained.

2) Synthesis of Fully Biobased bis(4-allyl-2-methoxyphenyl)furan-2,5-dicarboxylate 31.20 g Eugenol and 31.03 g triethylamine acting as base are dissolved in 200 mL dichloromethane to make solution A; at the temperature range of −4±1° C., 2,5-furan dicarboxylic acid chloride (19.30 g) is dissolved in 200 mL dichloromethane solution to get 2,5-furan dicarboxylic acid chloride solution, which is then slowly dropped into solution A; After dropwise addition is completed, the reaction solution is slowly heated and maintained at 30° C. for 2 h; after the reaction is over, removing the solvent under reduced pressure, followed by washing with deionized water and drying, successively, a fully biobased bis(4-allyl-2-methoxyphenyl)furan-2,5-dicarboxylate is obtained.

3) Preparation of the Biobased Epoxy Resin 22.42 g Bis(4-allyl-2-methoxyphenyl)furan-2,5-dicarboxylate is dissolved in 225 mL dichloromethane, then 35.5 g metachloroperbenzoic acid (85 wt %) is slowly added under stirring at 25° C. The reaction kept for 3 days, and then a filtrate is obtained after filtration, which is then washed with 84.03 g 10% $Na_2SO_3$, 70.66 g 10% $Na_2CO_3$ and deionized water successively; the organic layer is obtained by separating and dried over anhydrous sodium sulfate; dichloromethane is removed to obtain a yellow solid which is washed by diethyl ether to get a white solid.

Example 15

1) Synthesis of 2,5-Furan Dicarboxylic Acid Chloride 31.20 g 2,5-Furandicarboxylic acid, 59.48 g thionyl chloride and N,N-dimethylformamide (DMF, catalyst, 0.05 mL) are mixed; the reaction is carried out for 5 h at 80° C. with stirring, and then the mixture is naturally cooled to room temperature. After removing the thionyl chloride under reduced pressure and drying, 2,5-furan dicarboxylic acid chloride is obtained.

2) Synthesis of Fully Biobased bis(4-allyl-2-methoxyphenyl)furan-2,5-dicarboxylate 34.48 g Eugenol and 23.73 g triethylamine acting as base are dissolved in 500 mL dichloromethane to make solution A; at the temperature range of −1±1° C., 2,5-furan dicarboxylic acid chloride (19.30 g) is dissolved in 500 mL dichloromethane solution to get 2,5-furan dicarboxylic acid chloride solution, which is then slowly dropped into solution A; After dropwise addition is completed, the reaction solution is slowly heated and maintained at 30° C. for 4 h; after the reaction is over, removing the solvent under reduced pressure, followed by washing with deionized water and drying, successively, a fully biobased bis(4-allyl-2-methoxyphenyl)furan-2,5-dicarboxylate is obtained.

3) Preparation of the Biobased Epoxy Resin 22.42 g Bis(4-allyl-2-methoxyphenyl)furan-2,5-dicarboxylate is dissolved in 300 mL dichloromethane, then 40.6 g metachloroperbenzoic acid (75 wt %) is slowly added under stirring at 30° C. The reaction kept for 3 days, and then a filtrate is obtained after filtration, which is then washed with 126.04 g 10% $Na_2SO_3$, 105.99 g 10% $Na_2CO_3$ and deionized water successively; the organic layer is obtained by separating and dried over anhydrous sodium sulfate; dichloromethane is removed to obtain a yellow solid which is washed by diethyl ether to get a white solid.

Example 16

1) Synthesis of 2,5-Furan Dicarboxylic Acid Chloride 31.20 g 2,5-Furandicarboxylic acid, 59.48 g thionyl chloride and N,N-dimethylformamide (DMF, catalyst, 0.05 mL) are mixed; the reaction is carried out for 4 h at 80° C. with stirring, and then the mixture is naturally cooled to room temperature. After removing the thionyl chloride under reduced pressure and drying, 2,5-furan dicarboxylic acid chloride is obtained.

2) Synthesis of Fully Biobased bis(4-allyl-2-methoxyphenyl)furan-2,5-dicarboxylate 31.20 g Eugenol and 8.10 g trimethylamine, 10.34 g N-ethyldiisopropylamine, 7.91 g pyridine, which acted as base are dissolved in 200 mL dichloromethane to make solution A; at the temperature ranging from −5 to 0° C., 2,5-furan dicarboxylic acid chloride (19.30 g) is dissolved in 200 mL dichloromethane solution to get 2,5-furan dicarboxylic acid chloride solution, which is then slowly dropped into solution A; After dropwise addition is completed, the reaction solution is slowly heated and maintained at 30° C. for 2 h; after the reaction is over, removing the solvent under reduced pressure, followed by washing with deionized water and drying, successively, a fully biobased bis(4-allyl-2-methoxyphenyl)-furan-2,5-dicarboxylate is obtained.

3) Preparation of the Biobased Epoxy Resin 22.42 g Bis(4-allyl-2-methoxyphenyl)furan-2,5-dicarboxylate is dissolved in 300 mL dichloromethane, then 40.6 g metachloroperbenzoic acid (75 wt %) is slowly added under stirring at 25° C. The reaction kept for 3 days, and then a filtrate is obtained after filtration, which is then washed with 126.04 g 10% $Na_2SO_3$, 105.99 g 10% $Na_2CO_3$ and deionized water successively; the organic layer is obtained by separating and dried over anhydrous sodium sulfate; dichloromethane is removed to obtain a yellow solid which is washed by diethyl ether to get a white solid.

What we claim is:

1. A preparation method of a biomass-based epoxy resin, characterized in comprising the following steps:
   (1) by mole, mixing 100 parts of 2,5-furandicarboxylic acid, 150 to 250 parts of thionyl chloride and N,N-dimethylformamide catalyst and stirring to react at a temperature of 70 to 80° C. for 3 to 5 h, naturally cooling to room temperature, removing thionyl chloride by vacuum distillation, and drying to obtain 2,5-furan dicarboxylic acid chloride;
   (2) by mole, dissolving 190 to 210 parts of eugenol and 240 to 300 parts of tertiary amine in 3120 to 7800 parts of dichloromethane solvent to obtain eugenol solution; at a temperature of −5 to 0° C., adding a solution by 100 parts of said 2,5-furan dicarboxylic acid chloride dissolved in 3120 to 7800 parts of dichloromethane dropwise in said eugenol solution, after completion of dropwise addition, heating the reaction solution to the temperature of 20 to 30° C., and continuing the reaction for 2 to 4 h; and then removing dichloromethane under vacuum rotary evaporation, washing and drying to obtain bis(4-allyl-2-methoxyphenyl)furan-2,5-dicarboxylate;
   (3) by mole, dissolving 100 parts of said bis(4-allyl-2-methoxyphenyl)furan-2,5-dicarboxylate in 4680 to 9360 parts of dichloromethane, then adding 300 to 400 parts of metachloroperbenzoic acid in under stirring at the temperature of 20 to 30° C., continuing to react for 2 to 4 days, and then a filtrate is obtained after filtration; washing and removing the solvent in the filtrate, and then washing again to obtain a white solid, which is the biomass-based epoxy resin.

2. The preparation method of a biomass-based epoxy resin according to claim 1, wherein said tertiary amine is one of triethylamine, N-ethyl diisopropylamine, pyridine, or any combination thereof.

3. A biomass-based epoxy resin obtained by the preparation method according to claim 1.

* * * * *